United States Patent [19]
Edwards et al.

[11] Patent Number: 5,456,662
[45] Date of Patent: Oct. 10, 1995

[54] METHOD FOR REDUCING SNORING BY RF ABLATION OF THE UVULA

[76] Inventors: Stuart D. Edwards, 1681 Austin Ave., Los Altos, Calif. 94024; David L. Douglass, 545 Albion Ave., Woodside, Calif. 94062

[21] Appl. No.: 239,658

[22] Filed: May 9, 1994

Related U.S. Application Data

[63] Continuation-in-part of Ser. No. 929,638, Aug. 12, 1993, abandoned, and Ser. No. 12,370, Feb. 2, 1993, and Ser. No. 62,364, May 13, 1993, and Ser. No. 61,647, May 13, 1993, and Ser. No. 61,072, May 14, 1993.

[51] Int. Cl.$^6$ ..................................................... A61B 1/00
[52] U.S. Cl. ............................................................. 604/22
[58] Field of Search ........................... 604/20–22, 101, 604/102, 264, 272–274; 606/2–4, 6, 7, 10–17; 128/395–402; 607/1, 2

[56] References Cited

U.S. PATENT DOCUMENTS

| | | |
|---|---|---|
| 32,066 | 1/1886 | Leveen . |
| 1,879,249 | 9/1932 | Hansaker ............................. 604/280 |
| 1,950,788 | 3/1934 | Ewerhardt et al. . |
| 1,968,997 | 8/1934 | Drucker . |
| 2,008,526 | 7/1935 | Wappler et al. . |
| 2,022,065 | 11/1935 | Wappler . |
| 2,047,535 | 7/1936 | Wappler . |
| 2,118,631 | 5/1938 | Wappler . |
| 2,710,000 | 6/1955 | Cromer et al. . |
| 3,230,957 | 1/1966 | Seifert . |
| 3,339,542 | 9/1967 | Howell . |
| 3,556,079 | 1/1971 | Omizo et al. ............................. 128/2 |
| 3,595,239 | 7/1971 | Petersen . |
| 3,598,108 | 8/1971 | Jamshidi . |
| 3,682,162 | 8/1972 | Colyer . |
| 3,828,780 | 8/1974 | Morrison, Jr. . |
| 3,835,842 | 9/1974 | Iglesias . |
| 3,840,016 | 10/1974 | Lindemann . |
| 3,850,175 | 11/1974 | Iglesias . |

(List continued on next page.)

FOREIGN PATENT DOCUMENTS

| | | |
|---|---|---|
| 10858/92 | 8/1992 | Australia . |
| 0370890 | 5/1990 | European Pat. Off. . |
| 0453071 | 10/1991 | European Pat. Off. . |
| 0495443 | 7/1992 | European Pat. Off. . |

(List continued on next page.)

OTHER PUBLICATIONS

Standard Urology Product Catalog, CIRCON ACMI: Stanford (1992).
Chang, Raymond J. et al, American Heart Journal, 125: 1276–1283 (May, 1993).
Cosman, Eric R. et al., Sterostatic and Functional Neurosurgery, pp. 2490–2499 (Date Unknown).
Diasonics, Brochure DIA 2000 171 CRF May 1988.
Perinchery, Narayan, "Neoplasms of the Prostate Gland." pp. 378–409 (Date Unknown).
Urology 5th ed., Storz, Jan. 1992.
Transuretheral μwave Thermotherapy for Protatism: Early Mayo Foundation Experience: Blute, Mayo Clinic Proceedings: vol. 67 May 1992 pp. 417–421.
New Therapies for Benign Prostatic Hyperplasia, Editorial Bruskewitz, Mayo Clinic Proceedings vol. 67 May 1992 pp. 483–495.
Industry Strategies, Urology: "A Multi Billion Dollar Market . . ." Stephan Scala Nov. 19, 1991 pp. 1–32.
U.I. Dept. of Health and Human Services, MMWR 41: 401–404 vol. 41, No. 23, (Jun. 12, 1992).

*Primary Examiner*—C. Fred Rosenbaum
*Assistant Examiner*—Manuel Mendez
*Attorney, Agent, or Firm*—Oblon, Spivak, McClelland, Maier & Neustadt

[57] ABSTRACT

A medical ablation method for reducing snoring wherein a flexible RF electrode wire surrounded by an insulating sleeve axially moveable thereon is inserted into an uvula; the sleeve is retracted to expose a predetermined portion of the electrode; and RF energy is applied to the uvula tissue through the electrode to cause internal lesions in the uvula and reduce snoring.

4 Claims, 4 Drawing Sheets

U.S. PATENT DOCUMENTS

| | | |
|---|---|---|
| 3,858,577 | 1/1975 | Bass et al. . |
| 3,884,237 | 5/1975 | O'Malley et al. . |
| 3,924,628 | 12/1975 | Droegemueller et al. . |
| 3,939,840 | 2/1976 | Storz . |
| 3,942,530 | 3/1976 | Northeved . |
| 3,948,270 | 4/1976 | Hasson . |
| 3,991,770 | 11/1976 | Leveen . |
| 4,011,872 | 3/1977 | Komiya . |
| 4,119,102 | 10/1978 | Leveen . |
| 4,121,592 | 10/1978 | Whalley . |
| 4,136,566 | 1/1979 | Christensen . |
| 4,137,920 | 2/1979 | Bonnet . |
| 4,154,246 | 5/1979 | Leveen . |
| 4,204,549 | 5/1980 | Paglione . |
| 4,224,929 | 9/1980 | Furihata . |
| 4,228,809 | 10/1980 | Paglione ................................. 128/804 |
| 4,237,898 | 12/1980 | Whalley . |
| 4,267,828 | 5/1981 | Matsuo . |
| 4,295,467 | 10/1981 | Mann et al. . |
| 4,307,720 | 12/1981 | Weber, Jr. . |
| 4,311,145 | 1/1982 | Esty et al. . |
| 4,311,154 | 1/1982 | Sterzer et al. . |
| 4,312,364 | 1/1982 | Convert et al. . |
| 4,375,220 | 3/1983 | Matvias . |
| 4,397,314 | 8/1983 | Vaguine . |
| 4,402,311 | 9/1983 | Hattori . |
| 4,405,314 | 9/1983 | Cope . |
| 4,411,266 | 10/1988 | Cosman . |
| 4,448,198 | 5/1984 | Turner . |
| 4,452,236 | 6/1984 | Utsugi . |
| 4,470,407 | 9/1984 | Hussein ................................. 606/2 |
| 4,494,539 | 1/1985 | Zenitani et al. . |
| 4,552,554 | 11/1985 | Gould et al. . |
| 4,562,838 | 1/1986 | Walker . |
| 4,565,200 | 1/1986 | Cosman . |
| 4,568,329 | 2/1986 | Mahurkar . |
| 4,580,551 | 4/1986 | Siegmund et al. . |
| 4,594,074 | 6/1986 | Anderson et al. . |
| 4,601,296 | 7/1986 | Yerushalmi . |
| 4,612,940 | 9/1986 | Kasevich et al. . |
| 4,658,836 | 4/1987 | Turner . |
| 4,660,560 | 4/1987 | Klein . |
| 4,669,475 | 6/1987 | Turner . |
| 4,672,962 | 6/1987 | Hershenson . |
| 4,676,258 | 6/1987 | Inokuchi et al. . |
| 4,681,122 | 7/1987 | Winters et al. . |
| 4,682,596 | 7/1987 | Bales et al. . |
| 4,697,595 | 10/1987 | Breyer et al. . |
| 4,700,716 | 10/1987 | Kasevich et al. . |
| 4,706,681 | 11/1987 | Breyer et al. . |
| 4,709,698 | 12/1987 | Johnston et al. . |
| 4,719,914 | 1/1988 | Johnson . |
| 4,753,223 | 6/1988 | Bremer . |
| 4,765,331 | 8/1988 | Petruzzi et al. . |
| 4,769,005 | 9/1988 | Ginsburg et al. . |
| 4,774,949 | 10/1988 | Fogarty . |
| 4,776,086 | 10/1988 | Kasevich et al. . |
| 4,781,186 | 11/1988 | Simpson et al. . |
| 4,784,638 | 11/1988 | Ghajar et al. . |
| 4,785,829 | 11/1988 | Convert et al. . |
| 4,798,215 | 1/1989 | Turner . |
| 4,800,899 | 1/1989 | Elliott . |
| 4,805,616 | 2/1989 | Pao . |
| 4,813,429 | 3/1989 | Eshel et al. . |
| 4,817,601 | 4/1989 | Roth et al. . |
| 4,818,954 | 4/1989 | Flachenecker et al. . |
| 4,822,333 | 4/1989 | Lavarenne . |
| 4,823,791 | 4/1989 | D'Amelio et al. . |
| 4,823,812 | 4/1989 | Eshel et al. . |
| 4,860,744 | 8/1989 | Johnson et al. . |
| 4,865,047 | 9/1989 | Chou et al. . |
| 4,872,458 | 10/1989 | Kanehira et al. . |
| 4,887,615 | 12/1989 | Taylor . |
| 4,893,623 | 1/1990 | Rosenbluth . |
| 4,896,671 | 1/1990 | Cunningham et al. . |
| 4,898,577 | 2/1990 | Badger . |
| 4,905,667 | 3/1990 | Foerster et al. . |
| 4,906,230 | 3/1990 | Maloney et al. . |
| 4,907,589 | 3/1990 | Cosman . |
| 4,911,148 | 5/1990 | Sosnowski et al. . |
| 4,911,173 | 3/1990 | Terwilliger . |
| 4,919,129 | 4/1990 | Weber, Jr. et al. . |
| 4,920,978 | 5/1990 | Colvin . |
| 4,932,958 | 6/1990 | Reddy et al. . |
| 4,936,281 | 6/1990 | Stasz . |
| 4,940,064 | 7/1990 | Desai . |
| 4,943,290 | 7/1990 | Rexroth ................................. 606/49 |
| 4,946,449 | 8/1990 | Davis, Jr. . |
| 4,949,706 | 8/1990 | Thon . |
| 4,950,267 | 8/1990 | Ishihara et al. . |
| 4,955,377 | 9/1990 | Lennox et al. . |
| 4,961,435 | 10/1990 | Kitagawa et al. . |
| 4,966,597 | 10/1990 | Cosman . |
| 4,967,765 | 11/1990 | Turner et al. . |
| 4,982,724 | 1/1991 | Saito et al. . |
| 4,998,932 | 3/1991 | Rosen et al. . |
| 4,998,933 | 3/1991 | Eggers et al. . |
| 5,002,558 | 3/1991 | Klein et al. . |
| 5,003,991 | 4/1991 | Takayama et al. . |
| 5,007,437 | 4/1991 | Sterzer . |
| 5,007,908 | 4/1991 | Rydell . |
| 5,010,886 | 4/1991 | Passafaro et al. . |
| 5,026,959 | 6/1991 | Ito et al. . |
| 5,029,588 | 7/1991 | Yock et al. . |
| 5,030,227 | 7/1991 | Rosenbluth et al. . |
| 5,035,695 | 7/1991 | Weber, Jr. et al. . |
| 5,035,696 | 7/1991 | Rydell . |
| 5,045,056 | 9/1991 | Behl . |
| 5,045,072 | 9/1991 | Castillo . |
| 5,055,109 | 10/1991 | Gould et al. . |
| 5,057,105 | 10/1991 | Malone et al. . |
| 5,057,106 | 10/1991 | Kasevich et al. . |
| 5,057,107 | 10/1991 | Parins . |
| 5,059,851 | 10/1991 | Corl et al. . |
| 5,060,660 | 10/1991 | Gambale et al. . |
| 5,071,418 | 12/1991 | Rosenbaum ................................. 606/45 |
| 5,080,660 | 1/1992 | Buelna . |
| 5,083,565 | 1/1992 | Parins . |
| 5,084,044 | 1/1992 | Quint . |
| 5,100,423 | 3/1992 | Fearnot . |
| 5,108,415 | 4/1992 | Pinchuk et al. . |
| 5,109,859 | 5/1992 | Jenkins . |
| 5,116,615 | 5/1992 | Gokcen et al. . |
| 5,120,316 | 6/1992 | Morales et al. . |
| 5,122,137 | 6/1992 | Lennox ................................. 606/42 |
| 5,135,525 | 8/1992 | Biscoping et al. . |
| 5,150,717 | 9/1992 | Rosen et al. . |
| 5,170,787 | 12/1992 | Lindegren . |
| 5,178,620 | 1/1993 | Eggers et al. . |
| 5,179,962 | 1/1993 | Dutcher et al. . |
| 5,190,539 | 3/1993 | Fletcher et al. . |
| 5,195,965 | 3/1993 | Shantha . |
| 5,195,968 | 3/1993 | Lundquist et al. . |
| 5,197,963 | 3/1993 | Parins ................................. 606/41 |
| 5,201,732 | 4/1993 | Parins et al. . |
| 5,207,672 | 5/1993 | Roth . |
| 5,220,927 | 6/1993 | Astrahan et al. . |
| 5,222,953 | 6/1993 | Dowlatshahi . |
| 5,228,441 | 7/1993 | Lundquist . |
| 5,234,004 | 8/1993 | Hascoet et al. ................................. 607/102 |
| 5,235,964 | 8/1993 | Abenaim . |
| 5,249,585 | 10/1993 | Turner et al. ................................. 607/99 |

| | | |
|---|---|---|
| 5,254,088 | 10/1993 | Lundquist et al. |
| 5,257,451 | 11/1993 | Edwards et al. |
| 5,273,535 | 12/1993 | Edwards et al. |
| 5,275,162 | 1/1994 | Edwards et al. |
| 5,281,213 | 1/1994 | Milder et al. |
| 5,281,217 | 1/1994 | Edwards et al. |
| 5,281,218 | 1/1994 | Imran. |
| 5,287,845 | 2/1994 | Faul et al. |
| 5,290,286 | 3/1994 | Parins. |
| 5,293,868 | 3/1994 | Nardella. |
| 5,293,869 | 3/1994 | Edwards et al. |
| 5,299,559 | 4/1994 | Bruce et al. |
| 5,300,068 | 4/1994 | Rosar et al. |
| 5,300,069 | 4/1994 | Hunsberger et al. |
| 5,300,070 | 4/1994 | Gentelia et al. |
| 5,300,099 | 4/1994 | Rudie. |
| 5,301,687 | 4/1994 | Wong et al. |
| 5,304,134 | 4/1994 | Kraus et al. |
| 5,304,214 | 4/1994 | Deford. |
| 5,309,910 | 5/1994 | Edwards et al. |
| 5,313,943 | 5/1994 | Houser et al. |

FOREIGN PATENT DOCUMENTS

| | | |
|---|---|---|
| 521264A2 | 1/1993 | European Pat. Off. |
| 2848484 | 5/1979 | Germany. |
| 3218314 | 6/1983 | Germany. |
| 3844131 | 12/1988 | Germany. |
| 3838840 | 5/1990 | Germany. |
| 2121675 | 5/1990 | Japan. |
| 9007303 | 7/1990 | WIPO. |
| WO911213 | 8/1991 | WIPO. |
| 9116859 | 11/1991 | WIPO. |
| 9207622 | 5/1992 | WIPO. |
| 9210142 | 6/1992 | WIPO. |
| WO92/10142 | 6/1992 | WIPO. |
| 9221285 | 12/1992 | WIPO. |
| 9221278 | 12/1992 | WIPO. |
| 9304727 | 4/1993 | WIPO. |
| 9308756 | 5/1993 | WIPO. |
| 9308755 | 5/1993 | WIPO. |
| 9320893 | 10/1993 | WIPO. |
| 9320886 | 10/1993 | WIPO. |
| 9308757 | 10/1993 | WIPO. |
| 9320767 | 10/1993 | WIPO. |
| 9320768 | 10/1993 | WIPO. |
| WO93/25136 | 12/1993 | WIPO. |
| 9403759 | 2/1994 | WIPO. |
| 9404222 | 3/1994 | WIPO. |
| 9405226 | 3/1994 | WIPO. |
| 9406377 | 3/1994 | WIPO. |
| 9407446 | 4/1994 | WIPO. |
| 9407549 | 4/1994 | WIPO. |
| 9407411 | 4/1994 | WIPO. |
| 9407410 | 4/1994 | WIPO. |
| 9407441 | 4/1994 | WIPO. |
| 9407413 | 4/1994 | WIPO. |
| 9407412 | 4/1994 | WIPO. |

5,456,662

METHOD FOR REDUCING SNORING BY RF ABLATION OF THE UVULA

RELATIONSHIP TO COPENDING APPLICATIONS

This application is a continuation-in-part of applications Ser. No. 07/929,638 filed Aug. 12, 1993 and now abandoned, Ser. No. 08/012,370 filed Feb. 2, 1993 (allowed), Ser. No. 08/062,364 filed May 13, 1993 (allowed), Ser. No. 08/061,647 filed May 13, 1993 (allowed), and Ser. No. 08/061,072 filed May 14, 1993 (allowed), the entire contents of each of the above applications being hereby incorporated by reference.

FIELD OF THE INVENTION

This invention relates generally to a method for penetrating body tissues for medical purposes such as reducing tissue mass. In particular, the invention relates to a method which penetrates tissue of an uvula in order to reduce the size of the uvula which reduces snoring.

BACKGROUND OF THE INVENTION

Treatment of cellular tissues usually requires direct contact of target tissue with a medical instrument, usually by surgical procedures exposing both the target and intervening tissue to substantial trauma. Often, precise placement of a treatment probe is difficult because of the location of a target tissue in the body or the proximity of the target tissue to easily damaged, critical body organs, nerves, or other components.

Destruction of cellular tissues in situ has been used in the treatment of many diseases and medical conditions alone or as an adjunct to surgical removal procedures. It is often less traumatic than surgical procedures and may be the only alternative where other procedures are unsafe. Ablative treatment devices have the advantage of using a destructive energy which is rapidly dissipated and reduced to a non-destructive level by conduction and convection forces of circulating fluids and other natural body processes.

Microwave, radiofrequency, acoustical (ultrasound), and light energy (laser) devices, and tissue destructive substances have been used to destroy malignant, benign and other types of cells and tissues from a wide variety of anatomic sites and organs. Tissues treated include isolated carcinoma masses and, more specifically, organs such as the prostate, glandular and stromal nodules characteristic of benign prostate hyperplasia. These devices typically include a catheter or cannula which is used to carry a radiofrequency electrode or microwave antenna through a duct to the zone of treatment and apply energy diffusely through the duct wall into the surrounding tissue in all directions.

The copending applications disclose an ablative medical probe generally for penetrating body tissues for medical purposes and a radio frequency medical treatment with optical viewing capabilities.

Extending this ablative technology to the problem shared by millions of people who snore when sleeping has became viable. Prior methods to control snoring included devices which prevent the sleeper from rolling over onto the sleeper's back, devices which emit loud noises or generate electric shocks to the patient when snoring is detected, and so on. These prior art systems and methods only change the sleeper's body orientation, but do not solve the problem or even address the proximate cause of the patient's snoring. Many times it is not the sleeper/snorer who is affected, but the sleeper's bed partner who receives the brunt of the punishment.

OBJECTS AND SUMMARY OF THE INVENTION

It is an object of this invention to provide an RF medical ablation method which is used to ablate tissue within a patient's uvula to reduce the size of the uvula and reduce or eliminate snoring.

It is another object of the present invention to provide a method of reducing snoring by reducing uvula size which minimizes bleeding and trauma to surrounding tissues.

These objects, as well as others, are provided by a medical ablation method for ablating tissue within an uvula to reduce snoring in which a flexible RF electrode wire and an insulating sleeve axially moveable thereon are inserted into an uvula. The sleeve is retracted to expose a predetermined portion of said electrode. Radio frequency (RF) energy is applied to the tissue of said uvula to cause ablation of the tissue.

DETAILED DESCRIPTION OF THE INVENTION

In order to more fully understand the preferred embodiments of the present invention, a general view of a patient's mouth will be described with reference to FIG. 1.

Figure 1:
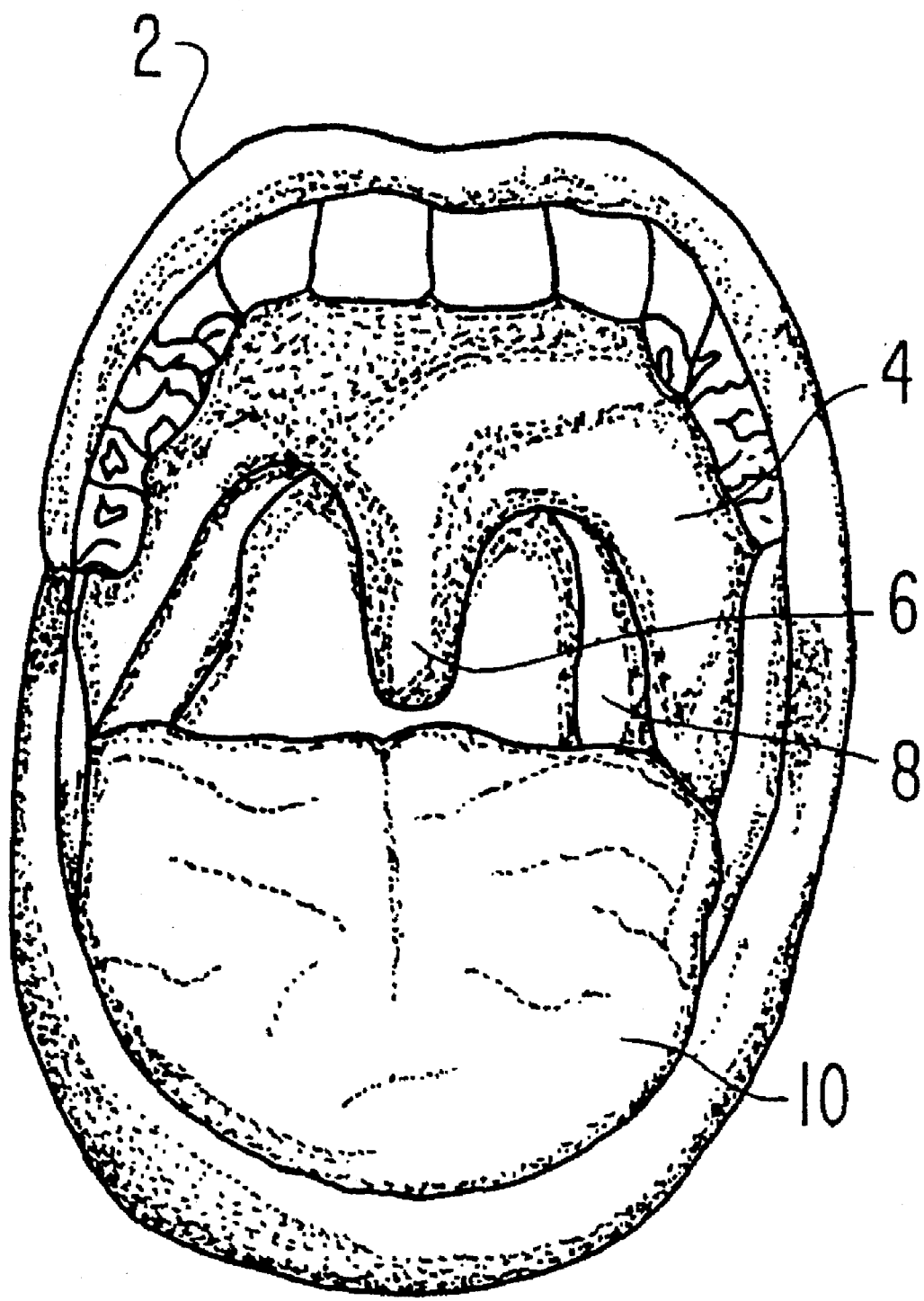
FIG. 1 is a front view of a person's mouth area showing the orientation of the uvula.

FIG. 1 shows a front view of a patient's mouth. Within the mouth 2 there is an upper part of the mouth known as a palate 4. A human palate can be defined as the roof of the mouth. The palate is divided into the hard palate and the soft palate. The hard palate is that portion of the roof of the mouth which is covered by bone (the maxillary bones). The soft palate is that portion of the palate behind the hard palate and is composed only of soft tissue. The coneshaped piece of tissue which hangs down from the soft palate in the back of the mouth is called the uvula 6.

In addition, for reference, a tongue 10 and a pair of tonsils 8 are shown in relation to the uvula 6.

Certain patients lie on their backs when sleeping and at certain times may breathe through their mouth. The movement of the air through the mouth to the lungs may cause the uvula 6 to vibrate and generate a hard, raspy sound that can be very loud at times. This sound is often referred to as a snore. The sleeping patient may not even be aware of snoring until informed by others. In certain other patients, the uvula 6 is large enough to hang down over the throat, effectively blocking the flow of air to the lungs. The patient then gasps for air and possibly wakes up startled and rolls over. Thus, snoring and its problems can be uncomfortable to the patient and certainly disquieting to the patient's bed partner as well.

Apart from the physical, external devices used to wake up the patient, or at least cause the snorer to roll over, there are surgical procedures that can be performed. A uvulectomy or partial uvulectomy can be performed to remove all or part of a patient's uvula. Any surgery, however, has its inherent risks, no matter how fit and healthy the patient may be. Also, the recovery time is extensive due to the bleeding and suturing that must be performed during the surgery. In addition, considerable pain and discomfort is caused to the patient. This conventional uvulectomy can be performed by normal scalpel excising or possibly by use of a strong laser light which is used to destroy part or all of the uvula tissue.

In order to decrease the pain, discomfort and recovery time of the patient, radio frequency (RF) or microwave ablative techniques can be used. In an RF ablative technique, an RF signal from an electrode placed inside the uvula tissue heats the tissue. The cells are heated to a point where the cells burst and die. In fact, the RF ablative technique causes a small lesion within the uvula which is absorbed by the body. Thus, no external bleeding occurs and no suturing is required. Also, the uvula size is decreased.

The medical ablation method utilized in this invention is uniquely superior for localized therapeutic ablation to remove or reduce undesired tissue masses in uvulas in order to reduce snoring.

To fully understand this method of reducing snoring using ablation, a description of an ablation device, as disclosed in the copending applications, follows.

Figure 2:
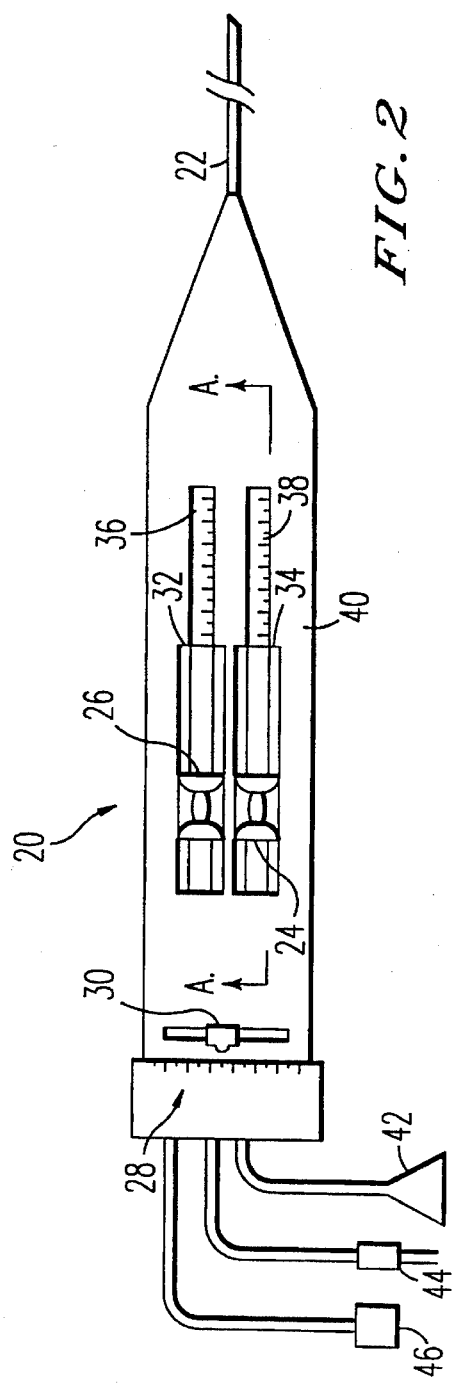
FIG. 2 is a planar view of a stylet ablation device of this invention.
Figure 3:
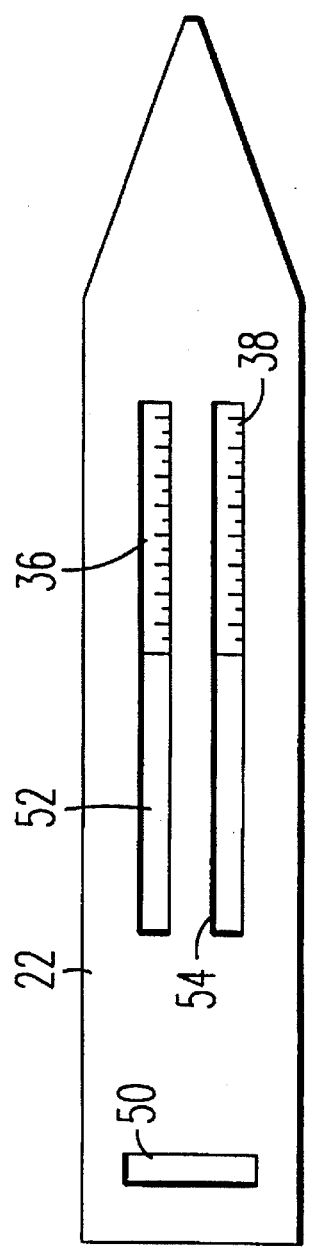
FIG. 3 is a top view of the handle top plate of the styler ablation device shown in FIG. 2.

Now, the particular structure of the ablation device will be described with reference to FIGS. 2 and 3. FIG. 2 is a planar view of the ablation device. The device generally has a handle portion 20 and a delivery tube portion 22. A stylet sleeve manual control tab 26 and a stylet electrode manual control tab 24 are mounted for sliding engagement in slots 52 and 54 of a handle top plate 40 (FIG. 3). Index markings 28 indicate the relative angle of orientation of the stylet with respect to a stylet angle indicator 30. The angle indicator 30 can be a bubble in a curved transparent tube, a weighted pivot dial indicator or an electronic angle indicator. The position of distal edges 32 and 34 of the tab slides 24 and 26 with their respective gauge reference strips 36 and 38 show the relative positions of a stylet electrode 58 and a sleeve 62 shown in FIGS. 3 to 5. A more detailed description of the operation of the tab slides and reference gauge is below.

Connectors for a fiber optic connector 42, an RF power connector 44, and an ohmic resistance connector 46 extend from the proximal end of the handle portion 20. The connectors connect the ablative device of the present invention to a light source, a power source and a detector, respectively.

FIG. 3 is a top view of the handle top plate 40 of the ablation device shown in FIG. 2. As discussed above, slots 52 and 54 receive the respective tabs 24 and 26 for sliding engagement therein. Slot 50 receives the stylet angle indicator 30. The reference strips 36, 38 are also shown.

Figure 4:
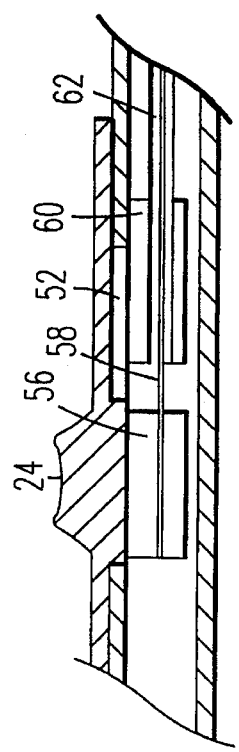
FIG. 4 is a fragmentary cross-sectional view of the manual control portion of the handle of the styler ablation device shown in FIG. 2, taken along the line A—A in FIG. 2.

Now the detailed description of the manual tabs 24,26 will be described. FIG. 4 is a fragmentary cross-sectional side view of the manual control portion of the handle of the stylet ablation device shown in FIG. 2, taken along the line A—A.

Since FIG. 4 is a side view, only the electrode manual control tab 24 is shown since the sleeve manual control tab 26 is directly behind the electrode manual control tab 24. The electrode manual control tab 24 is connected to an electrode connector 56. The electrode connector 56 is in turn connected to an electrode 58. Although not shown, the electrode 58 would also be electrically connected to the RF power connector 44 and the ohmic resistance connector 46. The electrode 58 slides inside of a sleeve 62. The sleeve 62 is connected to a sleeve connector 60 which in turn is connected to the sleeve manual control tab 26. Thus, the electrode 58 and the sleeve 62 slide relative to each other.

The electrode 58 is preferably made of any material which will conduct RF power. The sleeve 62 is preferably made of a highly conformable insulating plastic material such as polyamide. Now, the operation of the tabs 24, 26 will be described.

Simultaneous forward or rearward movement of both manual control tabs 24 and 26 cause the simultaneous advancement and retraction of both the electrode 58 and the sleeve 62. If the electrode manual control tab 24 is moved alone, then the electrode 58 slides within the sleeve 62 and either retracts into or extends out of the sleeve 62. Similarly, if only the sleeve manual control tab 26 is moved, the sleeve 62 slides over the electrode 58. The reference strips 36 and 38 provide reference points for controlled positioning of the electrode manual control tab 24 and the sleeve manual control tab 26, permitting precise, independent positioning of both the electrode 58 and the sleeve 62 for controlled ablation of the uvula as is explained in greater detail below.

Figure 5:
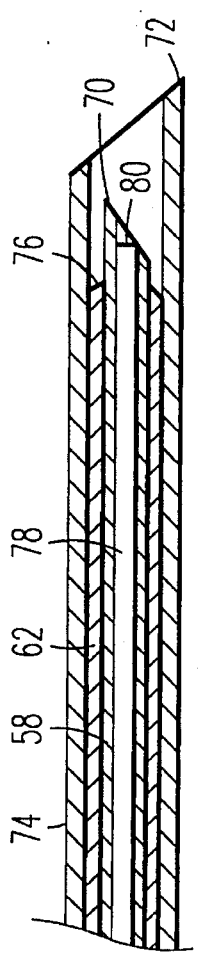
FIG. 5 is a fragmentary cross-sectional view of the tip of the styler ablation device such as that shown in FIG. 2 with the styler retracted into the tip.

FIG. 5 is a cross-sectional view of the tip of the ablation device such as that shown in FIG. 2 with the stylet retracted into the tip of a needle 74 for initial insertion to a position accessible with a straight needle. The electrode tip 70 is positioned behind the leading sharpened tip 72 of the needle 74, The insulating sleeve tip 76 is positioned just behind the leading edge of the electrode tip 70.

When the electrode 58 is a hollow tube, it can be a conduit for aspiration during treatment, liquid deliver, or in the embodiment shown, a housing for a fiber optic strand 78. The polished fiber optic tip 80 is positioned behind the electrode tip 70 to facilitate viewing of the tissue surrounding the electrode tip during insertion.

Figure 6:
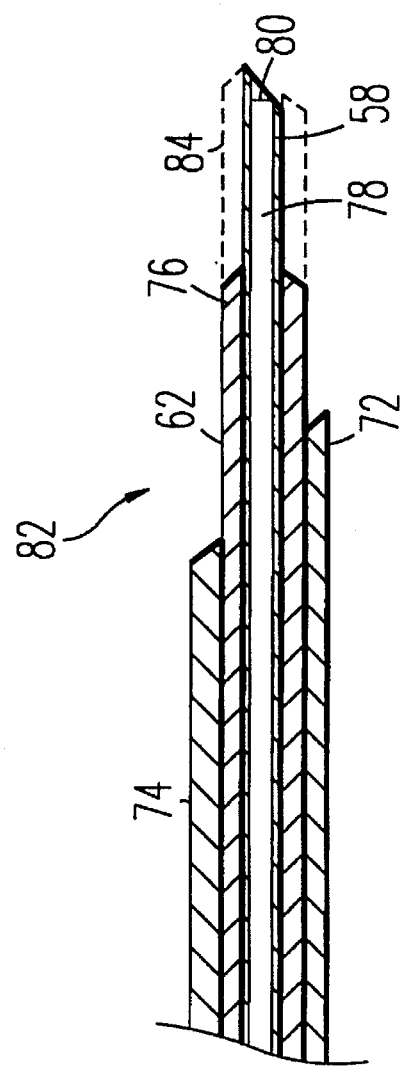
FIG. 6 is a fragmentary cross-sectional view of the tip of the styler ablation device shown in FIG. 2 with the electrode and sleeve extended from the tip.

FIG. 6 is a cross-sectional view of the tip of the stylet ablation device shown in FIG. 5 with the electrode and sleeve extended out of the needle 74. The sleeve 62 is initially in the dotted line position 84 in which it covers the electrode. Following insertion of the needle 72 into the body to the specific site to be ablated, the sleeve 62 is retracted from a selected portion of the electrode 58 to expose the specific electrode area required to form a lesion of the desired size. The retraction of the sleeve 62 is controlled by the sleeve manual control tab 26 as described above.

Figure 7:
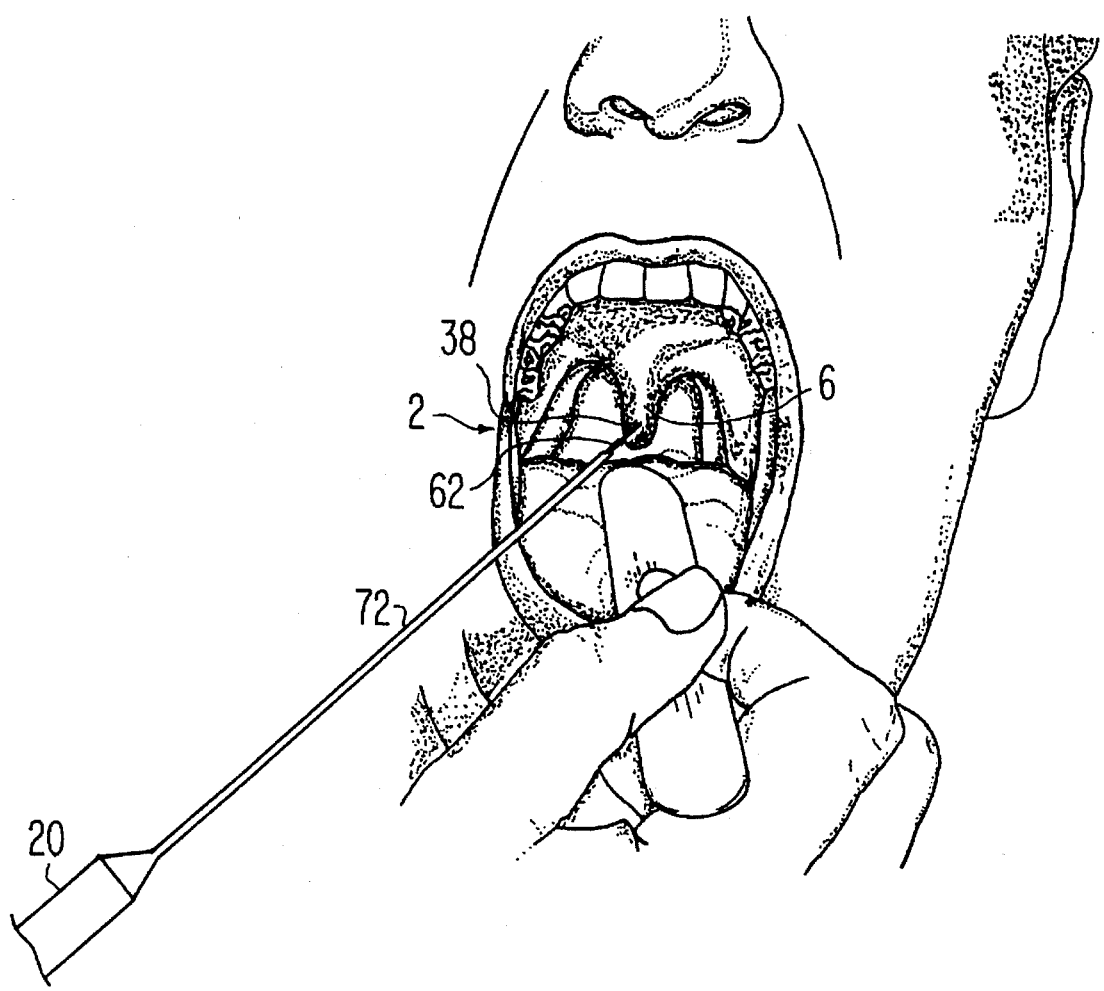
FIG. 7 is a front view of a patient's mouth wherein an uvula is being reduced by the ablative method of the present invention.

FIG. 7 shows a front view of a patient's mouth with the RF ablation device being used to treat an uvula 6 according to the present method. The patient opens his/her mouth 2 and the tongue is held down. The RF ablative device with the handle portion 20 is positioned so that the needle 72 is near the uvula 6. The sleeve 62 and electrode 58 are then extended out of the needle 72 and into the uvula 6. Then, the electrode 58 is exposed by a desired distance, depending on the amount of the uvula to be ablated. Then, RF or microwave energy is sent through the electrode 58 and causes an internal lesion within the uvula 6. Once this internal lesion is absorbed by the body, the size of uvula 6 decreases and further snoring problems are eliminated.

While the invention has been described with reference to specific preferred embodiments, it will be understood by those skilled in the art that various changes may be made and equivalents may be substituted for elements thereof without departing from the true spirit and scope of the invention. In addition, many modifications may be made without departing from the essential teachings of the invention.

We claim:

1. A method for medical ablation of tissue within a uvula to reduce snoring by reducing the size and mass of said uvula comprising the steps of:

a) inserting a needle into said uvula, said needle having an electrode enclosed within an insulating sleeve axially moveable thereon and bendable therewith;

b) retracting said sleeve from the terminus of the electrode to expose a predetermined electrode area for ablation; and d) applying RF energy to the tissue surrounding the exposed electrode area to effect ablation of said uvula tissue.

2. An ablation treatment method for reducing the mass of cellular tissue of the uvula in order to reduce snoring comprising:

a) introducing a cannula having a stylet lumen to the exterior of said uvula, the cannula having a distal end and a proximal end, the cannula having a control housing at its proximal end and an opening at its distal end, a flexible stylet with a sharp distal tip being enclosed within the stylet lumen of the cannula, the flexible stylet comprising an RF electrode having an insulating sleeve or coating extending along at least a portion thereof;

b) extending the flexible stylet from the distal end of the cannula into the mass of cellular tissue of the uvula to be reduced; and c) passing RF current from the stylet through the mass of cellular tissue of the uvula to be reduced sufficient to raise the temperature of cells of the mass of cellular tissue of the uvula for a time sufficient to cause death of the cells.

3. The ablation treatment method of claim 2 for reducing the mass of the uvula wherein the stylet electrode has an insulating sleeve longitudinally slidable on the electrode, the method including the steps of a) extending the flexible stylet and insulating sleeve from the distal end of the cannula into the mass of cellular tissue of the uvula to be reduced, and retracting the sleeve or extending the electrode beyond the sleeve to expose a preselected length of electrode in the uvula, thereby control ling the length of the lesion to be obtained in the treatment; and c) passing RF current from the stylet through the mass of cellular tissue of the uvula to be reduced sufficient to raise the temperature of cells of the mass of cellular tissue of the uvula to be reduced to above 47° C. for a time sufficient to cause death of the cells.

4. An ablation treatment method for reducing the mass of cellular tissue of the uvula in order to reduce snoring comprising:

a) introducing a cannula having a stylet lumen to the exterior of said uvula, the cannula having a distal end and a proximal end, the cannula having a control housing at its proximal end and an opening at its distal end, a flexible stylet with a sharp distal tip being enclosed within the stylet lumen of the cannula, the flexible stylet comprising a microwave antenna;

b) extending the distal end of the microwave antenna from the distal end of the cannula into the mass of cellular tissue of the uvula to be reduced; and c) energizing the microwave antenna at a power and for a time sufficient to raise the temperature of cells of the mass of cellular tissue of the uvula to be reduced to above 47° C. for a time sufficient to cause death of the cells.

\* \* \* \* \*

UNITED STATES PATENT AND TRADEMARK OFFICE
CERTIFICATE OF CORRECTION

PATENT NO. : 5,456,662

DATED : October 10, 1995

INVENTOR(S) : Stuart D. Edwards, David L. Douglass

It is certified that error appears in the above-indentified patent and that said Letters Patent is hereby corrected as shown below:

Col 2, line 31, change "styler" to –stylet—

Col 2, line 34, change "styler" to –stylet—

Col 2, line 38, change "styler" to –stylet—

Col 2, line 39, change "styler" to –stylet—

Col 2, line 41, change "styler" to –stylet—

Signed and Sealed this

Twelfth Day of August, 1997

Attest:

BRUCE LEHMAN

*Attesting Officer*      *Commissioner of Patents and Trademarks*